United States Patent [19]

Winston et al.

[11] Patent Number: 5,464,457
[45] Date of Patent: Nov. 7, 1995

[54] SOIL FUMIGATION WITH GASIFORM PESTICIDE

[75] Inventors: Anthony E. Winston, East Brunswick; Keith A. Jones, Lambertville, both of N.J.

[73] Assignee: Church & Dwight Co., Inc., Princeton, N.J.

[21] Appl. No.: 267,517

[22] Filed: Jun. 29, 1994

[51] Int. Cl.$^6$ .................. A01B 79/00; A01N 33/00
[52] U.S. Cl. ................... 47/58; 47/DIG. 10; 504/326
[58] Field of Search ................ 47/58, 9, DIG. 10; 71/142, 143; 424/719; 504/326, 327; 514/579

[56] References Cited

U.S. PATENT DOCUMENTS 4,726,144  2/1988  Young et al. .................. 47/58
4,819,374  4/1989  Gemgnani ..................... 47/58

Primary Examiner—David T. Fox
Assistant Examiner—Elizabeth F. McElwain
Attorney, Agent, or Firm—Charles B. Barris

[57] ABSTRACT

This invention provides a process for fumigating a plot of ground soil which involves dispersing a particulate ammonium carboxylate such as ammonium bicarbonate on or below the ground surface, followed by covering of the treated ground area with a tarpaulin to seal the ground surface from contact with the atmosphere. The tarpaulin covering is maintained on the ground surface for a sufficient time period to allow decomposition of the ammonium bicarbonate into a mixture of ammonia and carbon dioxide gases, and to effect fumigation of the covered plot with the generated gas mixture.

14 Claims, No Drawings

SOIL FUMIGATION WITH GASIFORM PESTICIDE

BACKGROUND OF THE INVENTION

Fumigants are commonly employed in the sterilization of hydroponic beds, in soil fumigation, and in the fumigation of structures such as warehouses, freight cars, and the like, to kill all living organisms therein.

The fumigant demand for agricultural and horticultural applications is projected to increase 3.7 percent per year to a volume of about 60 million dollars in 1995.

The growth rate of fumigant application has been limited because fumigants such as methyl bromide, chloropicrin and phosphine typically are pesticides in the form of poisonous gases which kill living organisms when absorbed or inhaled. Soil is fumigated to eliminate one or more pests such as insects, worms, bacteria, fungi, weed and grass seeds, and the like.

Methyl bromide, the most widely used fumigant, is a deadly gas which causes nausea and vomiting when inhaled by humans, and in severe cases inhalation can cause coma or death from respiratory failure.

Methyl bromide also is the largest single source of ozone-depleting bromine atoms in the stratosphere. In 1992 the parties to the Montreal Protocol On Substances That Deplete The Ozone Layer amended the treaty to require a freeze by 1995 on production of methyl bromide at 1991 levels. World production of methyl bromide in 1990 was about 63,000 metric tons.

In the United States, where the Clean Air Act requires that ozone-depleting substances be banned completely, the Environmental Protection Agency has set a Jan. 1, 2001 date for phaseout of methyl bromide. Producers and users of methyl bromide are opposing this ban, since there is a lack of readily available substitutes, and the ban will disrupt the growth, shipping and storage of important food crops such as tomatoes, strawberries, and citrus fruits.

There remains a high priority need for gaseous fumigants which can be utilized in agricultural and horticultural applications with relative safety to humans, and which do not have ozone-depleting reactivity.

SUMMARY OF THE INVENTION

Accordingly, it is an object of this invention to provide a method of fumigation with a gasiform means which in low concentrations is relatively safe for humans, and which does not interact with ozone in the stratosphere.

It is another object of this invention to provide a process for soil fumigation by treatment of the soil with an inorganic reagent which decomposes under ambient environment and soil conditions to release a mixture of ammonia and carbon dioxide gases that is effective for fumigation of the treated soil.

Other objects and advantages of the present invention shall become apparent from the accompanying description and examples.

DETAILED DESCRIPTION OF THE INVENTION

One or more objects of the present invention are accomplished by the provision of a process for fumigating a plot of ground soil which comprises (1) contacting the plot of soil with a particulate pesticide ingredient selected from the group consisting of ammonium bicarbonate, ammonium carbonate and ammonium carbamate; (2) covering the soil surface with a tarpaulin to seal the soil surface from the atmosphere; (3) maintaining the tarpaulin seal on the soil surface for a sufficient time period to allow decomposition of the pesticide ingredient to form ammonia and carbon dioxide gases, and to fumigate the covered plot of soil.

A present invention process embodiment is effective for complete eradication of living organisms in treated ground soil, such as fungi, nematodes, insects, and weeds. A present invention process embodiment provides particular advantage for the control of infectious phytopathogenic fungi which thrive under acidic soil conditions, such as *Sclerotinia sclerotiorum*.

The term "ammonium carboxylate" as employed hereinafter refers to ammonium salts such as ammonium bicarbonate, ammonium carbonate and ammonium carbamate which contain an ammonium carboxylate structure:

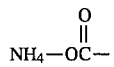

The ammonium carboxylate reagent which is employed in the process decomposes at a slow rate at 20° C. The rate of decomposition increases as the ambient temperature increases.

If the invention process is practiced outdoors in bright sunlight and at an air temperature which elevates to 30° C. or higher during the daytime, the ground which is sealed under the tarpaulin cover absorbs radiant energy, and the ground temperature can elevate to 35° C. or higher.

The mixture of ammonia and carbon dioxide gases generated under the tarpaulin cover is heavier than air, so that the air content of the covered soil is displaced by the heavier gases. Eradication of living organisms in the treated soil is caused by the depletion of oxygen in the soil, and by the toxic effects of the ammonia and carbon dioxide gases.

An ammonium carboxylate such as ammonium bicarbonate per se exhibits herbicidal, insecticidal and nematocidal activity, and is a potent fungicide under the invention process soil treatment conditions. There is an extended presence of ammonium carboxylate in the covered ground soil since the ammonia and carbon dioxide can recombine with water to form ammonium carboxylate. The ammonium carboxylate decomposition reaction to ammonia and carbon dioxide is in equilibrium with the ammonia and carbon dioxide reaction to ammonium carboxylate.

The particulate ammonium carboxylate which is employed in the invention process for soil fumigation preferably has an average particle size between about 20–1000 microns. Powders with a particle size less than about 20 microns tend to be dusty under field application conditions, and they have a tendency to cake. A preferred particle size distribution is in the range between about 40–200 microns.

Optionally, the ammonium carboxylate can be employed in the form of slow-release granules or prills or the like, if the fumigation process is intended to extend over a time period longer than several days. One means of providing extended-release ammonium carboxylate is by the use of urea in the presence or absence of urease enzyme. The urea hydrolysis reaction can be accelerated by the addition of alkali metal carbonate to increase the pH.

The particulate ammonium carboxylate fumigant can be applied to the ground soil either alone or in combination with other ingredients, such as additional pesticide ingredients, fertilizers, inert diluents, anti-caking agents, and the like.

The particulate ammonium carboxylate can be used in admixture with between about 0.1–15 weight percent of an anti-caking ingredient, based on the admixture weight.

The anti-caking ingredient is selected from particulate inorganic and organic compounds which are chemically unreactive with the ammonium bicarbonate. A selected compound preferably has a particulate size distribution less than about 100 microns in diameter.

Suitable anti-caking ingredients include silicious compounds, magnesium compounds, $C_{10}$–$C_{22}$ fatty acid polyvalent metal salt compounds, and the like.

Illustrative of anti-caking ingredients are attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the like. An anti-caking ingredient also can function as an inert diluent when employed in a quantity between about 0.2–5 parts by weight per part by weight of ammonium bicarbonate.

Preferred anti-caking ingredients include magnesium oxide, magnesium silicate, and the magnesium and aluminum salts of $C_{10}$–$C_{22}$ fatty acids such as palmitic acid, stearic acid and oleic acid.

A preferred type of particulate ammonium carboxylate ingredient is an admixture of ammonium bicarbonate with between about 0.05–80 weight percent of particulate ammonium carbonate, based on the admixture weight. Ammonium carbonate is more basic than ammonium bicarbonate, and decomposes more rapidly under the process fumigation conditions with the release of a higher level of ammonia gas. The generated ammonia gas can react with acidic elements in the soil, and become incorporated in the soil. The ammonium entity can function as a fertilizer when the fumigated plot of soil subsequently is cultivated with an agricultural crop.

As a further embodiment, the particulate ammonium carboxylate in the process can be admixed with between about 0.1–1 part by weight of particulate urea per part by weight of ammonium carboxylate, based on the admixture weight. As an alternative physical combination of ingredients, the particulate ammonium carboxylate can be surface-coated with between about 0.05–30 weight percent of urea, based on the ammonium carboxylate weight, as illustrated in Example II of the specification.

The urea ingredient can function both as a fertilizer and as a slow-release source of ammonia. Urea hydrolyzes to generate ammonia and bicarbonate ions, and the net product result is the formation of ammonium bicarbonate in situ and the release of ammonia:

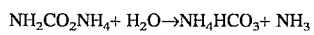

The ammonium bicarbonate formation in situ also can be accomplished by employing a urea acid salt such as urea hydrochloride, in combination with ammonium carbonate. The hydrochloride and carbonate react to form ammonium bicarbonate salt in situ. An additional or alternative means of increasing the ammonia release rate from urea is by utilizing an enzyme such as urease to catalyze the amide hydrolysis.

In the practice of the invention process, the particulate ammonium carboxylate, either alone or in combination with other constituents as described hereinabove, can be dispersed on the surface of the ground soil which is being fumigated. The heavier-than-air ammonia and carbon dioxide mixture of gases which is generated under the tarpaulin will diffuse into the ground soil by displacing air.

If penetration of the fumigant gases down to 10–15 inches in depth is an objective, then preferably the introduction of particulate ammonium carboxylate is coordinated with a ground plowing operation. Other means of penetrating ammonium carboxylate below the ground surface is by utilizing farm equipment which normally is used for embedding the soil with seeds, seedlings, fertilizers, and the like.

After the particulate ammonium carboxylate has been distributed by dispersion on the ground surface or by soil penetration means in the designated land area, a tarpaulin is placed as a covering over the ammonium carboxylate-treated ground surface, and the tarpaulin edges are anchored to the ground to form a partially or fully sealed enclosure on the ground surface. A suitable soil fumigation tarpaulin generally has a thickness between about 0.75–5 mils.

The tarpaulin typically is a plastic film sheeting of low density polyethylene or high density polyethylene, or a blend of low density and high density polyethylenes. The tarpaulin functions as a barrier to any substantial diffusion of ammonia and carbon dioxide gases into the environment. It is advantageous to utilize a clear plastic film tarpaulin, since this type of tarpaulin increases the amount of radiant energy which reaches the soil during daylight hours. The absorbed heat trapped under the tarpaulin provides a "greenhouse effect".

Depending on the quantity of particulate ammonium carboxylate which is employed, and the type of soil pathogens being eradicated, the soil surface is sealed with the tarpaulin for a time period between about 10–120 hours, or longer. The quantity of dispersed particulate ammonium carboxylate typically will vary in the range between about 25–750 pounds per acre and typically will be in the range between about 100–400 pounds per acre.

In another embodiment the present invention contemplates a fumigation process in which the ammonium carboxylate is distributed on the ground surface as an aqueous solution having a concentration between about 1–15 weight percent of ammonium carboxylate. The tarpaulin is placed immediately as a sealed covering over the treated ground area, and the tarpaulin seal is maintained until sterilization of the treated soil is completed.

In another embodiment the present invention contemplates a fumigation process in which the ammonium carboxylate is applied to pest-infested soil as an aqueous solution, and the treated soil is not covered with a tarpaulin. The uncovered soil requires a heavy application of between about 200–1000 pounds per acre of ammonium carboxylate to obtain a sterilized soil which is pest-free.

A solution with an increased concentration of ammonium carboxylate between about 15–25 weight percent can be obtained by dissolving the ammonium bicarbonate in an aqueous solution of ammonium hydroxide having a concentration between about 2–20 weight percent of ammonium hydroxide. Optionally, between about 0.05–20 weight percent of ammonium carbonate can be included in the solution, based on the combined weight of bicarbonate and carbonate ingredients. A concentrated aqueous slurry of ammonium carboxylate also can be employed advantageously.

The addition of between about 0.1–3 weight percent of a surfactant to an aqueous ammonium carboxylate solution increases the effectiveness of the solution when applied to soil, by increasing the penetration and the uniform wetting of the soil by the applied solution. Suitable surfactants include those listed in publications such as U.S. Pat. No. 3,541,213. One type of surfactant is an alkali metal or ammonium salt of a $C_8$–$C_{22}$ aliphatic-containing carboxylate, sulfonate, sulfate or phosphate.

Illustrative of other surfactant types are dioctyl sodium sulfosuccinate, cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; and the like.

The following examples are further illustrative of the present invention. The components and specific ingredients are presented as being typical, and various modifications can be derived in view of the foregoing disclosure within the scope of the invention.

EXAMPLE I

This Example illustrates the preparation of free-flowing pesticide powders in accordance with the present invention.

A

A blend of the following weight ratio of particulate ingredients is prepared in a cone mixer:

|  | Parts |
| --- | --- |
| ammonium bicarbonate | 99 |
| magnesium oxide | 1 |

The formulation blend is in the form of a lump-free powder.

B

A blend of the following weight ratio of particulate ingredients is prepared in a cone mixer:

|  | Parts |
| --- | --- |
| ammonium bicarbonate | 50 |
| ammonium carbonate | 5 |
| urea | 20 |
| potassium carbonate | 24.5 |
| magnesium silicate | 0.5 |

The formulated blend is a free-flowing powder which passes through a 100 mesh screen.

EXAMPLE II

This Example illustrates the preparation of a free-flowing urea-coated ammonium bicarbonate powder in accordance with the present invention.

Urea (1000 g) is dissolved in ethanol (2 liters). Ammonium bicarbonate (150 mesh, 5000 g) is suspended in the ethanol solution with stirring.

The ethanol solvent is removed by evaporation under vacuum. A dry powder is obtained, in which the urea is adsorbed as microcrystals on the surface of the ammonium bicarbonate particles.

The dry powder is blended with finely divided magnesium oxide (500 g) to provide a free-flowing powder composition.

EXAMPLE III

This Example illustrates the effectiveness of the present invention process for pre-emergence weed control.

A free-flowing pesticide composition corresponding to the Example I(B) formulation is prepared. The pesticide composition is tested at a concentration which is equivalent to about 180 pounds of ammonium bicarbonate per acre of treated soil.

Pesticide composition aliquots are admixed with soil which is disposed in 7.5 inch plastic pots that respectively contain weed seeds of velvet leaf, jimsonweed, switchgrass, barnyard grass, and green foxtail. Each pot opening is sealed with clear polyethylene film (1.5 mils).

The pots are set outdoors with full exposure to ambient conditions of light and temperature. Over a period of three days, the average daytime temperature is 28° C. (6 AM–6 PM), and the temperature of the soil under the plastic film reaches an average peak temperature of 42° C.

The percent control of each weed type is determined three weeks after treatment in comparison with untreated controls. The results indicate essentially 100 percent control of each weed type germination.

When the comparative tests are conductd with treated soil in pots which are not sealed with plastic film, about 20 percent of the seeds survive the treatment and germinate.

EXAMPLE IV

This Example illustrates the effectiveness of the present invention process for control of fungi in cultivated soil.

An upscale quantity of a free-flowing pesticide composition corresponding to the Example II formulation is prepared.

Three adjacent plots of farmland (110'×40' respectively) are prepared for test purposes. The ground soil in the plots is infected with *Sclerotinia sclerotiorum* and Fusarium.

The pesticide composition is distributed on the ground surface of two plots in a concentration which is equivalent to about 120 pounds of ammonium bicarbonate per acre. Both plots are plowed to a depth of about eight inches, and then harrowed. The untreated third plot is also plowed and harrowed.

The pesticide-treated first plot is covered with a clear polyethylene sheet (1.5 mils), which has its edges anchored to the ground surface to seal and isolate the covered plot area. The pesticide-treated second plot is left exposed.

Over a test period of five days, the average daytime temperature is 26° C. (6 AM–6 PM) in the covered plot, and the covered soil reaches an average peak temperature of 38° C.

Test cores of soil samples are collected from the three plots. There is no evidence of fungus infection in the soil samples of the covered pesticide-treated first plot. The soil samples from the uncovered pesticide-treated second plot exhibit a diminished content of the two fungi, but there is evidence of residual infection. The soil samples from the control plot exhibit an increased population of the two fungi.

Similar fungicidal results are obtained when the ammonium bicarbonate is applied as a 15 weight percent aqueous solution (having a content of 5 weight percent ammonium hydroxide) to an adjacent plot of farmland, with test conditions equivalent to those described hereinabove. After application of the aqueous solution, the plot then is covered with the same type of clear polyethylene sheet as described hereinabove.

EXAMPLE V

This Example illustrates the preparation and application of an aqueous pesticide formulation in accordance with the present invention.

A free-flowing pesticide composition is prepared by blending the following particulate ingredients:

|  | Parts |
| --- | --- |
| ammonium bicarbonate | 99.05 |
| sodium dioctyl sulfosuccinate | 0.40 |
| sodium caprylate | 0.25 |
| magnesium oxide | 0.30 |

The free-flowing powder is dissolved in water to form a 15 weight percent aqueous solution. The solution is applied by knives to a six inch soil depth at an application rate of 500 pounds of ammonium bicarbonate per acre.

Following procedures similar to those in Example IV, collected soil samples are found to be free of fungus infection.

EXAMPLE VI

This Example illustrates the effectiveness of the present invention process for control of fungi, nematodes and insects in cultivated soil.

A 15 weight percent aqueous solution is prepared in accordance with the pesticide formulation of Example V.

The aqueous solution is applied to soil at the rate of 400 gallons per acre to a soil depth of six inches through knives spaced at one foot intervals. The treated soil area is covered with a clear plastic tarpaulin for 48 hours.

The average daytime temperature is 26° C. (6 AM–6 PM), and the covered soil reaches an average peak temperature of 38° C. Test cores of soil samples indicate that the treated soil is sterile. There is a complete absence of fungi, nematodes, insects, and weeds.

When similar tests are conducted without a tarpaulin cover on the treated soil, the fungi and weeds are substantially but not completely eradicated. The nematodes and insects are completely eradicated.

What is claimed is:

1. A process for fumigating a plot of ground soil which comprises (1) contacting the plot of soil with a particulate pesticide ingredient selected from the group consisting of ammonium bicarbonate, ammonium carbonate and ammonium carbamate; (2) covering the soil surface with a tarpaulin to seal the soil surface from the atmosphere; (3) maintaining the tarpaulin seal on the soil surface for a sufficient time period to allow decomposition of the pesticide ingredient to form ammonia and carbon dioxide gases, and to fumigate the covered plot of soil.

2. A process in accordance with claim 1 wherein the pesticide ingredient has an average particle size between about 20–1000 microns, and is in admixture with between about 0.1–15 weight percent of an anti-caking ingredient, based on the admixture weight.

3. A process in accordance with claim 1 wherein the particulate pesticide ingredient is in admixture with between about 0.2–5 parts by weight of particulate inorganic diluent per part by weight of pesticide ingredient.

4. A process in accordance with claim 1 wherein the particulate pesticide ingredient is dispersed on the soil surface.

5. A process in accordance with claim 1 wherein the particulate pesticide ingredient is dispersed below the soil surface.

6. A process in accordance with claim 1 wherein the particulate pesticide ingredient is in admixture with between about 0.1–1 part by weight of particulate urea per part by weight of pesticide ingredient, based on the admixture weight.

7. A process in accordance with claim 1 wherein the particulate pesticide ingredient is surface-coated with between about 0.05–30 weight percent of urea, based on the pesticide ingredient weight.

8. A process in accordance with claim 1 wherein the tarpaulin is clear plastic sheeting.

9. A process in accordance with claim 1 wherein soil surface is sealed with the tarpaulin for a time period between about 10–120 hours.

10. A process in accordance with claim 1 wherein the ambient atmospheric temperature during the daylight hours of the fumigation period is between about 5°–40° C.

11. A process for fumigating soil which comprises (1) contacting the soil with an aqueous solution of a pesticide ingredient selected from the group consisting of ammonium bicarbonate, ammonium carbonate and ammonium carbamate; (2) covering the soil surface with a tarpaulin to seal the soil surface from the atmosphere; (3) maintaining the tarpaulin seal on the soil surface for a sufficient time period to allow decomposition of the pesticide ingredient to form ammonia and carbon dioxide gases, and to fumigate the covered soil.

12. A process in accordance with claim 11 wherein the aqueous solution contains between about 1–15 weight percent of the pesticide ingredient.

13. A process in accordance with claim 11 wherein the aqueous solution contains between about 15–25 weight percent of pesticide ingredient, and between about 2–20 weight percent of ammonium hydroxide.

14. A process in accordance with claim 11 wherein a concentrated aqueous slurry of pesticide ingredient is employed in step (1).

* * * * *